US009856343B2

(12) United States Patent
Palmese et al.

(10) Patent No.: US 9,856,343 B2
(45) Date of Patent: Jan. 2, 2018

(54) RENEWABLE BIO-BASED (METH)ACRYLATED MONOMERS AS VINYL ESTER CROSS-LINKERS

(71) Applicants: Drexel University, Philadelphia, PA (US); The United States of America as represented by the Secretary of the Army, Washington, DC (US)

(72) Inventors: Giuseppe R. Palmese, Hainesport, NJ (US); John Joseph La Scala, Wilmington, DE (US); Joshua Matthew Sadler, Middle River, MD (US); Anh-Phuong Thy Lam, Newark, DE (US)

(73) Assignees: Drexel University, Philadelphia, PA (US); The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 15/474,101

(22) Filed: Mar. 30, 2017

(65) Prior Publication Data

US 2017/0298165 A1   Oct. 19, 2017

Related U.S. Application Data

(63) Continuation of application No. 15/130,165, filed on Apr. 15, 2016, now Pat. No. 9,644,059, which is a continuation of application No. 14/237,170, filed as application No. PCT/US2012/050235 on Aug. 10, 2012, now abandoned.

(60) Provisional application No. 61/521,981, filed on Aug. 10, 2011.

(51) Int. Cl.
| | |
|---|---|
| *C08F 222/20* | (2006.01) |
| *C08F 122/20* | (2006.01) |
| *C08F 220/32* | (2006.01) |
| *C07D 493/04* | (2006.01) |
| *C08F 224/00* | (2006.01) |
| *C08F 124/00* | (2006.01) |

(52) U.S. Cl.
CPC .......... *C08F 222/20* (2013.01); *C07D 493/04* (2013.01); *C08F 122/20* (2013.01); *C08F 124/00* (2013.01); *C08F 220/32* (2013.01); *C08F 224/00* (2013.01); *C08F 2220/325* (2013.01)

(58) Field of Classification Search
CPC ..... C07D 493/04; C08F 124/00; C08F 224/00
USPC ...................................................... 526/268
See application file for complete search history.

(56) References Cited

U.S. PATENT DOCUMENTS

| | | |
|---|---|---|
| 3,041,300 A | 6/1962 | Morrison |
| 3,272,845 A | 9/1966 | Zech et al. |
| 6,121,398 A | 9/2000 | Wool et al. |
| 6,825,242 B2 | 11/2004 | Sulzbach et al. |
| 7,619,056 B2 | 11/2009 | East et al. |
| 7,723,461 B1 | 5/2010 | Wagener et al. |
| 2003/0139489 A1 | 7/2003 | Sulzbach et al. |
| 2009/0018300 A1* | 1/2009 | Bloom .............. C08G 61/12 527/102 |
| 2009/0275715 A1 | 11/2009 | Boyles et al. |
| 2011/0048739 A1 | 3/2011 | Blair et al. |
| 2012/0092426 A1 | 4/2012 | Chopra et al. |

FOREIGN PATENT DOCUMENTS

| | | |
|---|---|---|
| DE | 952092 | 11/1956 |
| GB | 586141 A | 3/1947 |
| JP | 2003306490 A | 10/2003 |
| JP | 2003313188 A | 11/2003 |
| WO | WO2009155020 A2 | 12/2009 |
| WO | WO2011048739 A1 | 4/2011 |
| WO | WO2013066461 A2 | 5/2013 |

OTHER PUBLICATIONS

European Office Action; dated Jun. 13, 2017 for EP Application No. EP12845143.2.
International Preliminary Report on Patentability; dated Feb. 20, 2014 for corresponding PCT Application No. PCT/US2012/050235.
Xu, M. et al., "Samarium diiodide induced asymmetric synthesis of γ-butyrolactone using chiral auxiliaries derived from isosorbide and isomannide," Chinese Journal of Chemistry, 1998, vol. 16, No. 6, pp. 561-564.
Xuchen, T., et al., "Systhesis and Characterization of a New Liquid Crystal Polymer," Journal of Textile Research, 2011, vol. 32, No. 1, pp. 20-24.
Lukaszczyk, J., et al., "Investigation on Synthesis and Properties of Isosorbide Based Bis-GMA Analogue," Journal of Materials Science: Materials in Medicine, vol. 23, No. 5, 2012, pp. 1149-1155.
European Search Report; dated Mar. 20, 2015 for the corresponding EP Application No. EP12845143.2.
European Office Action; dated Feb. 26, 2016 for the corresponding EP Application No. EP12845143.2.
Non-Final Office Action; dated Jun. 14, 2016 for U.S. Appl. No. 15/130,165.

(Continued)

*Primary Examiner* — Ling Choi
*Assistant Examiner* — Chun-Cheng Wang
(74) *Attorney, Agent, or Firm* — Mendelsohn Dunleavy, P.C.

(57) ABSTRACT

Anhydrosugar-based monomers prepared from isosorbide, isomannide, and isoidide and resin systems containing these anhydrosugar-based monomers that are partially to fully bio-based, which may produce materials having properties that meet or exceed the properties of similar petroleum derived vinyl ester resins.

21 Claims, 3 Drawing Sheets

(56) References Cited

OTHER PUBLICATIONS

Notice of Allowance; dated Jan. 3, 2017 for U.S. Appl. No. 15/130,165.
Supplemental Notice of Allowance; dated Jan. 23, 2017 for U.S. Appl. No. 15/130,165.

* cited by examiner

RENEWABLE BIO-BASED (METH)ACRYLATED MONOMERS AS VINYL ESTER CROSS-LINKERS

RELATED APPLICATION DATA

This application is a continuation of U.S. patent application Ser. No. 15/130,165, filed Apr. 15, 2016, which is a continuation of U.S. patent application Ser. No. 14/237,170, filed May 14, 2014, which claims priority to International Application No. PCT/US12/050235, filed Aug. 10, 2012, and U.S. Provisional Application No. 61/521,981, filed Aug. 10, 2011, the entire disclosure of which is hereby incorporated by reference as if set forth fully herein.

STATEMENT OF GOVERNMENT INTEREST

This invention was made with government support under Cooperative Agreement No. W911NF-0-06-2-0013 awarded by the U.S. Army Research Laboratory. The government has certain rights in the invention.

BACKGROUND OF THE INVENTION

1. Field of the Invention

The present invention relates to bio-based monomers derived from non-petroleum celluloses or carbohydrates with a core scaffold of isosorbide, isomannide or isoidide, and their use for producing renewable vinyl resin systems.

2. Description of the Related Technology

Vinyl ester resins are thermosetting polymers that are commonly used in variety of applications ranging from adhesives to the resin matrices for fiber reinforced composites. There are many desirable features for vinyl ester resins, such as strength, toughness, low cost, low weight, and particular viscosities for processing, which are the reasons that vinyl ester resins have such wide acceptance in military and commercial uses.

Viscosity is a key factor for determining the utility of vinyl ester resins because lower viscosity resins are easier to work with and may be prepared using a larger range of methods. Petroleum-based vinyl ester resins are typically high molecular weight species that are often an extremely viscous fluids or solids. They require reactive diluents in order to reduce the resin viscosity so that the resins can be processed. Typical reactive diluents, such as styrene, are generally regarded as Hazardous Air Pollutants (HAPs) and/or Volatile Organic Compounds (VOCs) whose use is controlled by the Environmental Protection Agency (EPA). Large research efforts have been devoted to finding ways to eliminate or reduce the use of these highly hazardous reactive diluents.

Another factor that prevents vinyl ester resins' wider commercial use is that they are frequently derived from petroleum products. Petroleum is a commodity with well-known price volatility. The environmental costs of using petroleum are also very high.

Vinyl ester resins derived from renewable sources cam reduce dependency on petroleum and have quickly become an imperative for continued use and development of thermosetting polymers and composites. Bio-refining of material based on converting biomass into vinyl ester products has been successfully developed. For example, bio-refining of triglycerides and carbohydrates have produced a wealth of new fine chemicals that are useful for the development of bio-based polymers. Fatty acids and triglycerides have also been successfully developed into materials ranging from toughening agents and plasticizers to reactive diluent replacements.

U.S. Pat. No. 6,121,398 (Wool et al.) discloses functionalized triglycerides derived from plant oil that are polymerizable and their use to produce high modulus polymers. The functionalized triglycerides may be produced via several different chemical synthesis routes. For example, epoxidized triglyerides may be produced and converted to resilient rubbers by control of the molecular weight and cross-link density. The resultant rubbers can be used as rubber toughening agents in rigid composites. In the examples of this patent, acrylated base resins are prepared by reacting the epoxidized triglycerides with acrylic materials such as acrylic acid. The thermosetting resins prepared by this method are said to have properties similar to commercially available bisphenol-A vinyl ester resins. Other functionalized triglycerides are described in U.S. Pat. No. 6,825,242 and U.S. patent application publication nos. US 2003/0139489 and US 2009/0275715.

Besides triglycerides, anhydrosugars derived from cellulose or carbohydrates, such as isosorbide, isomannide and isoidide, have also been explored for use as reactive monomers. These anhydrosugars are useful building blocks because they provide a rigid bicyclic core structure that can be developed into resins. For example, anhydrosugar, or bis-anhydrohexitols, have been fashioned into epoxy resins by forming the corresponding glycidyl ethers, as described in U.S. Pat. No. 3,041,300 (Zech, et al.) and U.S. Pat. No. 3,272,845 (Morrison, et al.). U.S. Pat. No. 7,619,056 (Jaffe, et al.) describes a different synthesis process whereby the glycidyl ethers of these anhydrosugars can be obtained, and subsequently cured with polyamines to form thermosets.

However, anhydrosugars have not been successfully used to produce low viscosity thermosetting vinyl ester resins. Reactive diluents such as styrene are still commonly used for reducing viscosity of these bio-based resins. Commercial practice involves reducing the styrene content in the resin to about 33 wt % styrene, which makes the resin barely acceptable for composite manufacturing applications. In addition, reducing the styrene content significantly reduces the toughness of these resins.

Therefore, there is a need in the field to provide bio-based vinyl ester resins with excellent processabilty, acceptable toughness and a reduced dependency on reactive diluents.

SUMMARY OF THE INVENTION

In the first aspect, the invention is directed to novel anhydrosugar-based monomers that are derived from isosorbide, isomannide, or isoidide. These monomers may be use as low viscosity cross-linkers for thermoset resins. These monomers may also be used to produce neat polymer for vinyl ester resins.

In another aspect, the invention relates to the use of anhydrosugar-based monomers for the preparation of low viscosity vinyl ester resins.

In yet another aspect, the invention relates to the use of anhydrosugar-based monomers as viscosity modulators and Tg enhancers in vinyl ester resins, thereby allowing a reduction in the reactive diluent concentration while maintaining suitable polymer toughness.

DETAILED DESCRIPTION OF THE PREFERRED EMBODIMENT(S)

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

Figure 1:
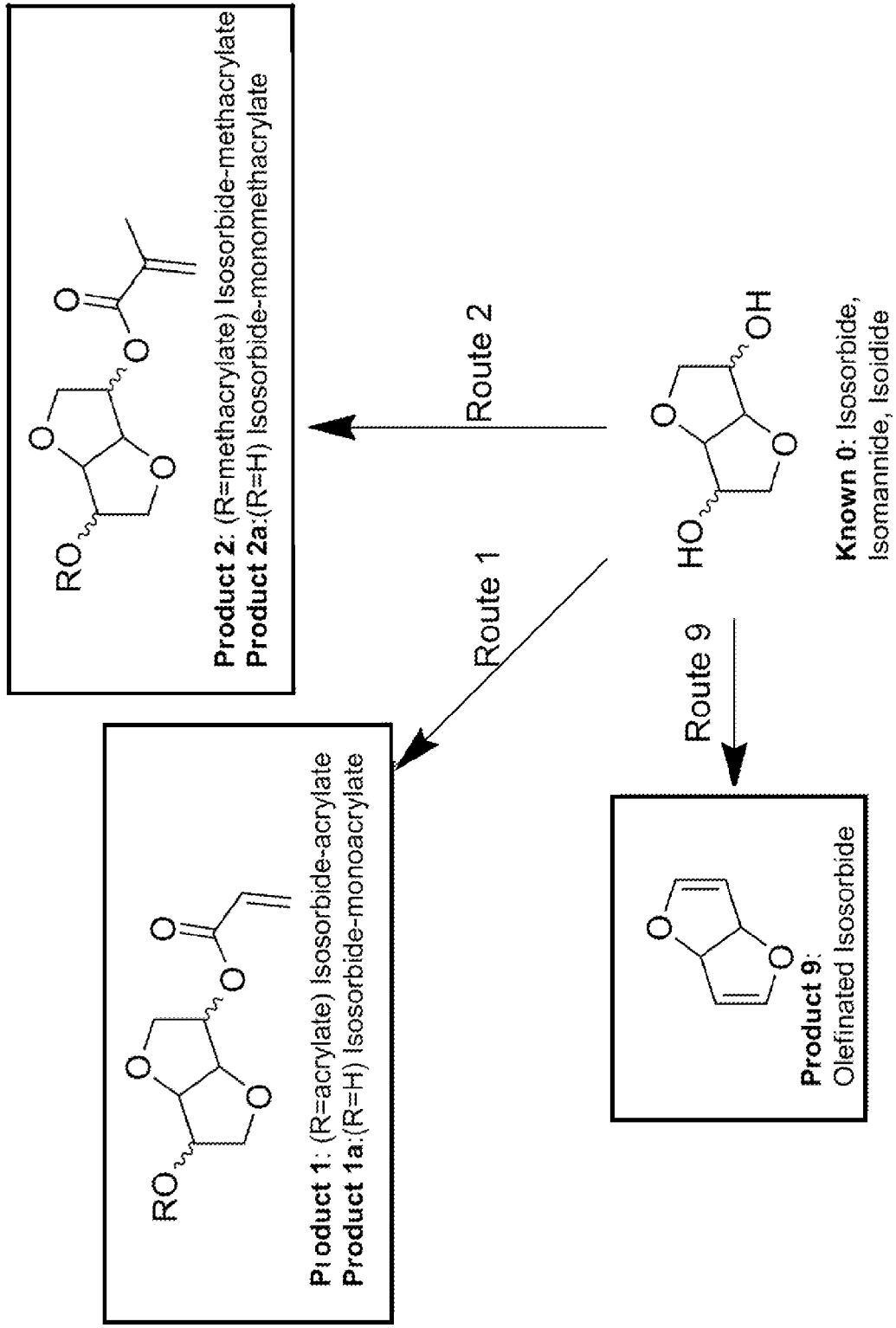
FIG. 1 shows the synthetic routes for anhydrosugar-based monomers, using isosorbide as illustrative examples. Either isomannide or isoidide may be used in place of isosorbide in these synthetic routes.
Figure 1:
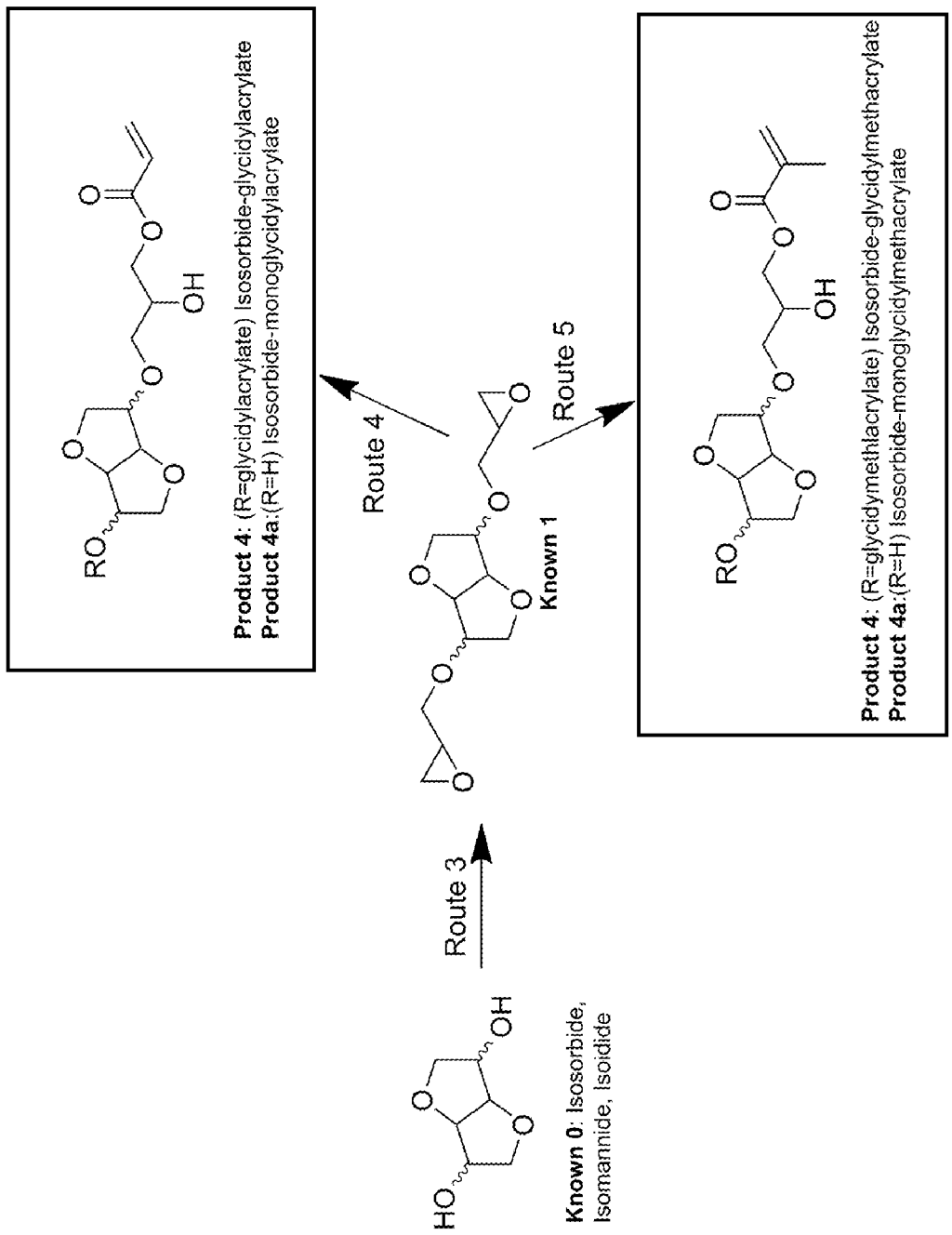
Figure 1:
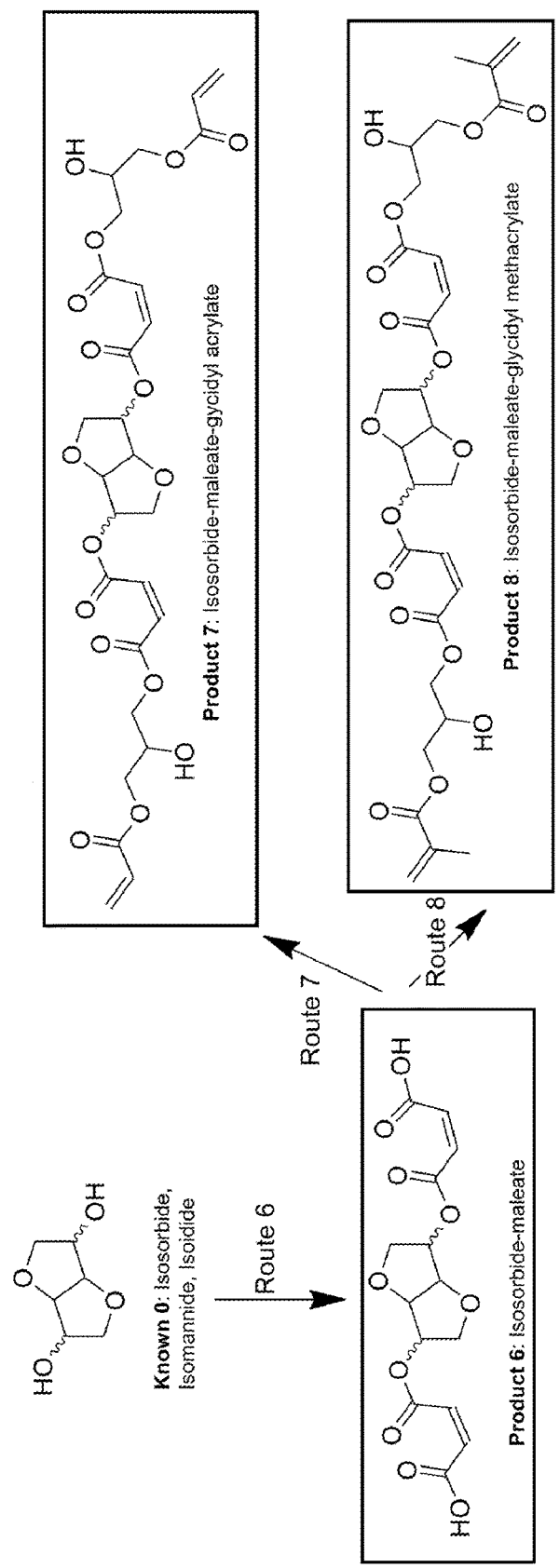

In one aspect, the present invention relates to the development of anhydrosugar-based monomers for vinyl ester resin systems. The monomers are derived from plant cellulose or carbohydrates, which are completely renewable sources. Eight of these monomers derived from isosorbide are shown in FIG. 1 as Products 1-2 and Products 4-9. Other monomers are derived from isomannide or isoidide using the same synthetic routes. These monomers may be used as low viscosity cross-linkers for thermosetting vinyl ester resins, which can replace petroleum-based vinyl ester thermosetting resins for nearly all of their applications.

One important feature of these anhydrosugar-based monomers is their relatively low molecular weight due to their confined core structure resulting from the limited carbon chain length of these naturally occurring sugars. The low molecular weights of these anhydrosugar-based monomers can be used to reduce the overall viscosity of vinyl ester resins containing them, which, in turn, can reduce the dependency on reactive diluents. This has the advantage of reducing the use of reactive diluents, yet still producing vinyl ester resins with acceptable toughness and processability.

A number of different synthetic routes may be employed to produce these anhydrosugar-based monomers. FIG. 1 shows some of the applicable synthetic routes, using isosorbide as illustrative example. Similar synthetic routes are available for the other two anhydrosugars: isomannide and isoidide. The starting materials, isosorbide, isomannide, or isoidide (Known 0 in FIG. 1), are industrially refined from naturally occurring sugars by a two-step process: 1) reducing glucose, mannitose, or idose, respectively; and 2) subjecting the reduced glucose, mannitose or idose to an acid catalyzed dehydration to produce a fused bicyclic ring system. The anhydrosugars have formulae:

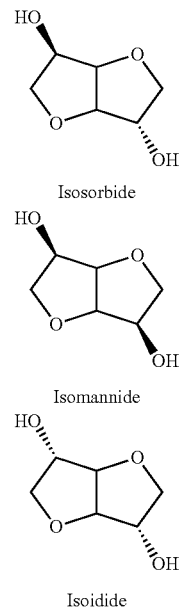

Isosorbide

Isomannide

Isoidide

In synthetic route 1 of FIG. 1, the anhydrosugars are acrylated to produce an acrylated monomer, Products 1 and 1a, which are capable of free radical polymerization. Products 1 and 1a have the formulae:

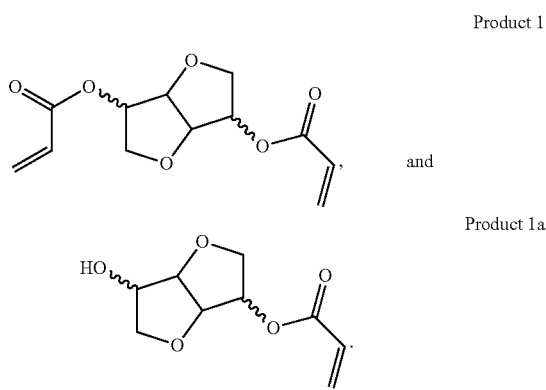

Product 1 and

Product 1a

Several exemplary methods may be used to produce Product 1 from anhydrosugars. One method involves acylation of the hydroxyl groups of anhydrosugars using either acryloyl chloride or acryl anhydride and a base catalyst in an aprotic solvent. A second method involves esterification of anhydrosugars using acrylic acid, catalyzed using either acidic or basic conditions. A third method involves transesterification of anhydrosugars using methyl acrylate, catalyzed by either an acid or base catalyst. The reacting ester can be any combination of a parent acid that is an acrylate and a matching alcohol used to form the ester which is 1-8 carbon atoms in length. The small molecule alcohol of 1-8 carbon atoms is selected since it has a relatively low boiling point and can easily evaporate as the reaction progresses.

Synthetic route 2 of FIG. 1 is similar to synthetic route 1 in that the anhydrosugars are functionalized using a variety of different methods to produce a methacrylated derivative, Products 2 and 2a, which are capable of free radical polymerization. Products 2 and 2a have the formulae:

Product 2

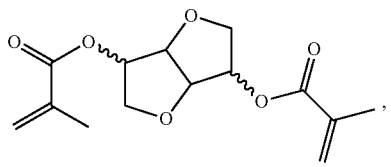

and

Product 2a

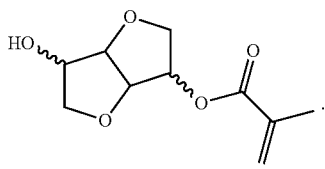

Several exemplary methods may be used to produce Product 2 from anhydrosugars. One method involves acylation of the hydroxyl groups of anhydrosugars using either methacryloyl chloride or methacryl anhydride, catalyzed by a base catalyst in an aprotic solvent. A second method involves esterification of anhydrosugars using methacrylic acid, catalyzed by either acidic or basic conditions. A third method involves transesterification of anhydrosugars using methyl methacrylate, catalyzed by either an acid or base catalyst. The reacting ester can be any combination of a parent acid that is a methacrylate and a matching alcohol used to form the ester which is 1-8 carbon atoms in length. The small molecule alcohol of 1-8 carbon atoms is selected since it has a relatively low boiling point and can easily evaporate as the reaction progresses.

Synthetic route 3 of FIG. 1 produces an intermediate referred to as Product 3 or Known 1. The formula of Product 3 is:

Product 3

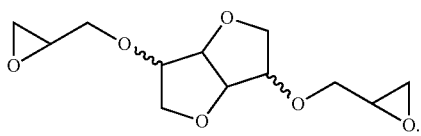

This process is well known in the art, as described in, for example, U.S. Pat. No. 3,041,300 (Zech, et al.), U.S. Pat. No. 3,272,845 (Morrison, et al.), and U.S. Pat. No. 7,619,056 (Jaffe, et al.). Both of Products 4 and 5 are derived from this intermediate Known 1.

In synthetic route 4 of FIG. 1, Known 1 is treated with acrylic acid in the presence of a chromium based catalyst, such as AMC-2™ (Aerojet chemicals, Rancho Cordova, Calif.). The reaction is carried out at 90-105° C., with 2.0-5.0 wt % catalyst based on the total weight of the reaction mixture. Alternatively, the synthetic route 4 can be carried out using another suitable method. For example, reaction of Known 1 with acrylic acid in refluxing acetonitrile catalyzed with 12-25 mol % tetrabutylammonium bromide (TBAB), based on the number of moles of Known 1, will also result in Products 4 and 4a. This reaction can be monitored using acid number titrations until the desired acid number (AN) is reached and the reaction is complete. Another synthetic route for Products 4 and 4a is by a reaction between Known 0 of FIG. 1 and glycidyl acrylate. Products 4 and 4a have the formulae:

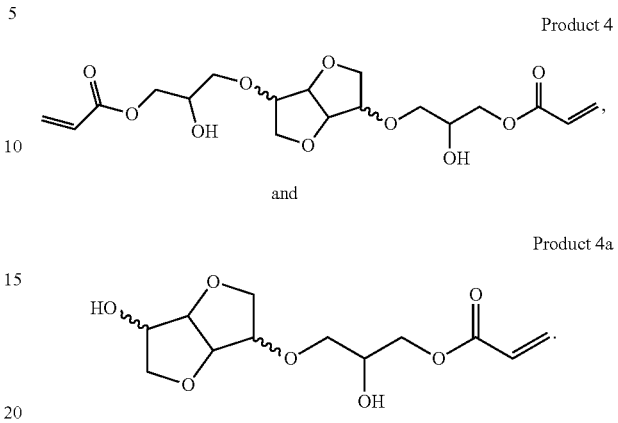

In synthetic route 5 of FIG. 1, Known 1 is treated with methacrylic acid in the presence of a chromium based catalyst, such as AMC-2™ (Aerojet chemicals, Rancho Cordova, Calif.). The reaction is carried out at 90-105° C., with 2.0-5.0 wt % catalyst based on the total weight of the reaction mixture. Alternatively, Known 1 may be reacted with methacrylic acid in refluxing acetonitrile catalyzed with 12-25 mol % TBAB, based on the number of moles of Known 1. The resultant product is also Products 5 and 5a. This reaction can be monitored for completion using acid number titrations. Products 5 and 5a have the formulae:

Product 5

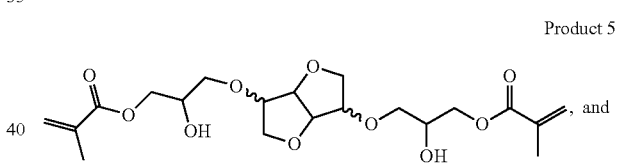

, and

Product 5a

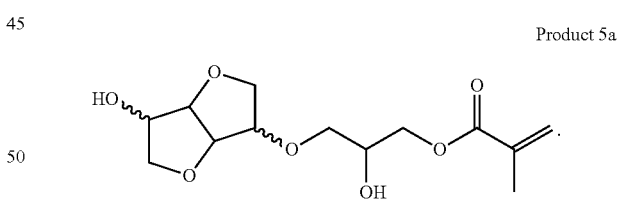

Both of synthetic routes 4 and 5 open the epoxide rings on Known 1 to produce two free hydroxyl groups. These hydroxyl groups can be further functionalized with a number of different R groups. Examples of such R groups include acrylates, methacrylates, maleates, glycidyl ethers, or an alkyl, alkenyl or aryl substituent.

Synthetic route 6 of FIG. 1 is maleination of Known 0, which results in Product 6. In an exemplary reaction, Known 0 and maleic anhydride are melted together to form a homogeneous solution before adding a base catalyst and stirring at 75-95° C. for 2-5 hours. Product 6 can be used as a cross-linking agent, or it can be used as an intermediate for synthetic routes 7 and 8. Product 6 has the formula:

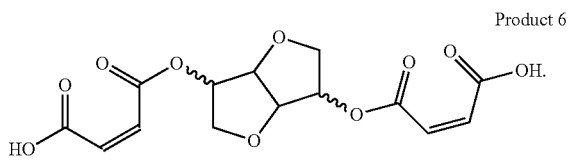 [SMILES: O=C(O)/C=C\C(=O)OC1COC2C(OC(=O)/C=C\C(=O)O)COC12]

Product 6

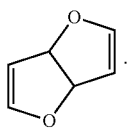

Product 9

Synthetic routes 7 and 8 in FIG. 1 are analogous reactions wherein the treatment of Product 6 with a glycidyl vinyl ester, such as glycidyl acrylate or glycidyl methacrylate, produces Products 7 and 8, respectively. Use of the AMC-2™ catalyst in 0.5-3.0 wt % based on the total reaction mixture at low temperatures results in the formation of the desired product in excellent yields.

Alternatively, synthetic routes 7 and 8 can be carried out by TBAB catalyzed refluxing in acetonitrile. Reaction of Product 6 with a glycidyl vinyl ester, such as glycidyl acrylate or glycidyl methacrylate, in refluxing acetonitrile catalyzed with 2.5-20 mol % TBAB, based on the number of moles of Product 6, results in Products 7 and 8, respectively. This reaction can be monitored using acid number titrations until the desired acid number is reached and the reaction is complete. Product 7 has the formula:

The anhydrosugar-based monomers of the present invention have been characterized both chemically and physically. Infrared (IR) spectra for each individual monomer show absorbance peaks in the expected regions for key functional groups. Nuclear Magnetic Resonance ($^1$H NMR) experiments have also been used for structure confirmation. Chemical shifts for $^1$H NMR peaks are in agreement for each monomer and appear as expected. Physical properties of these monomers have also been tested and found to have melting points ranging from and exhibited viscosities in the starting at 120 cP to being unmeasurable without the aid or reactive diluent. Overall, these anhydrosugar-based monomers are low-cost, have a low viscosity and low volatility and possess multiple polymerizable sites. These monomers are also reactive with other vinyl ester monomers.

The anhydrosugar-based monomers of the present invention are ideally suited for use as vinyl ester cross-linkers.

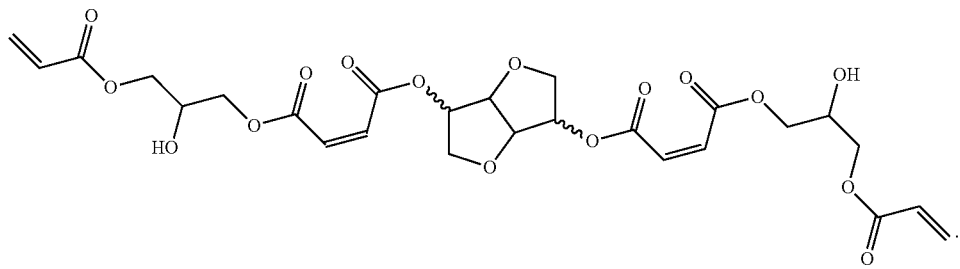

Product 8 has the formula:

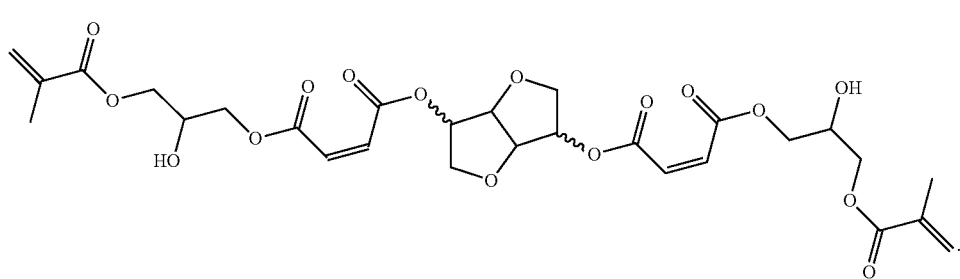

Product 8

The reaction of Product 6 with glycidyl vinyl esters results in the opening of an epoxide ring and the formation of two free hydroxyl groups in Products 7 and 8. These hydroxyl groups can be further functionalized with a number of different R groups. Examples of such R groups include acrylates, methacrylates, maleates, glycidyl ethers, or an alkyl, alkenyl or aryl substituent.

Synthetic route 9 of FIG. 1 is the dehydration of Known 0, where Known 0 is dissolved in solvent, preferably with a boiling point greater than 100° C., with 5-35 mol %, based on the starting sugar, of acid catalyst and gently heated to between 50-80° C. to distill Product 9. Product 9 has the formula:

The anhydrosugar-based monomers exhibit suitable viscosities for producing new resins with low viscosity that require a minimal amount of reactive diluent. These anhydrosugar-based monomers can partially or completely replace petroleum-based cross-linkers used in the manufacture of vinyl ester resins. Preferably, the anhydrosugar-based monomeric cross-linkers of the present invention are used as the only vinyl ester cross-linkers in the vinyl ester resin systems.

In another aspect of the present invention, the anhydrosugar-based monomers may be used as viscosity modulators. The anhydrosugar-based monomers have a confined core structure resulting from the limited carbon chain length of the naturally occurring sugars from which they are derived. The small core of these anhydrosugar monomers results in relatively low molecular weight anhydrosugar-based monomers that can be employed to reduce the overall viscosity of vinyl ester resins because of their low molecular weight in comparison with petroleum-based, relatively high molecule weight cross-linkers. Thus, the monomers of the present invention are well-suited for modulating the viscosity of vinyl ester resins by varying the amount of anhydrosugar-based monomer used in blends with petroleum-based, high viscosity cross-linkers.

In yet another aspect of the present invention, the anhydrosugar-based monomers may be used as glass transition temperature (Tg) enhancers in vinyl ester resins to the desired level while also decreasing the viscosity. Because many of the bio-based reactive diluents have poor Tg's (homopolymers typically have Tg's below 0° C.), as compared to styrene, the anhydrosugar-based monomers of the present invention may be used to raise the Tg's of a resin system using bio-based reactive diluents without increasing the overall viscosity. On the other hand, the Tg of of vinyl ester resins increases as the anhydrosugar-based monomer concentration increases. Thus, the anhydrosugar-based monomers may be used as Tg enhancers for vinyl ester resin systems. The ideal Tg for vinyl ester resins can be varied over a wide range of, for example, 40-250° C., depending on the intended end use and the temperatures at which the resins will be used. The amount of anhydrosugar-based monomer in a particular vinyl ester resin system may be varied in order to achieve the desired Tg for the vinyl ester resin.

In yet another aspect of the present invention, the anhydrosugar-based monomers may be polymerized with themselves to form novel vinyl ester polymers. In one embodiment, a vinyl ester resin system by be made from a single, pure anhydrosugar-based monomer of present invention. In another embodiment, two or more different anhydrosugar-based monomers may be polymerized with one another to form vinyl ester co-polymers. The anhydrosugar-based monomers can be polymerized to form linear, branched, hyperbranched, and cross-linked polymers. The neat monomer can be treated with a free-radical initiator, with or without a promoter, in order to induce curing to form the polymers. These polymers have properties comparable to petroleum-based vinyl ester derived polymers and exhibit similar stiffness and toughness and can have Tg's ranging from 0-270° C.

A binary resin system may also be formed from one or more anhydrosugar-based monomers blended with a reactive diluent to produce vinyl ester resins. In such binary resin systems, the compositions will typically contain 50-80% by weight of anhydrosugar-based monomers, and 2-50%, and, more preferably, 20-50% by weight of reactive diluents, with all weights being based on the weight of the product resin mixture. The reactive diluents may be petroleum or bio-based. These resins have been found to have a very low viscosities ranging from 5.0-110,000 cP, which would make them ideal for liquid molding, composite layups and vacuum assisted resin transfer molding (VARTM) processing, as well as a wide range of other applications.

In general, compositions may include 1-100% by weight of anhydrosugar-based vinyl ester monomers, 0-99% by weight of reactive diluent, such as the reactive diluents described herein, with all weights being based on the total weight of the resin product.

The binary resin systems may be cured using a free-radical initiator, in the presence or absence of a promoter, to produce bio-derived co-polymers that have similar properties to polymeric materials produced from petroleum products. These polymers possess stiffness and toughness equivalent to petroleum derived vinyl ester resins, with Tg's ranging from 45-235° C.

Exemplary reactive diluents suitable for use in the present invention are petroleum-based and bio-based compounds with a single polymerizable site. Suitable petroleum-based reactive diluents include, but are not limited to, styrene, 2-hydroxymethacrylate, methyl methacrylate, methyl acrylate, aryl-methacrylates, aryl-acylates, aliphatic methacrylates, aliphatic acrylates. Suitable bio-based reactive diluents include, but are not limited to, furfuryl methacrylate, tetrahydrofurfuryl methacrylate, furfuryl acrylate, tetrahydrofurfuryl acrylate, furioc acid glycidyl methacrylate (FA-GM), furioc acid glycidyl acrylate and methacyrlated lauric acid, methacrylated octanoic acid, methacrylated fatty acids, and acrylated fatty acids.

A ternary resin system may also be formed by blending one or more anhydrosugar-based monomers with vinyl ester resins and reactive diluents. Ternary compositions will typically include up to 60%, more preferably, 5-15% by weight of reactive diluent(s) and 40-99%, more preferably, 85-95% by weight of vinyl ester cross-linker monomers, wherein the composition of the cross-linker monomers is 15-99% by weight anhydrosugar-based monomers and 1-70% by weight of vinyl ester resin and/or unsaturated polyester monomer, more preferably, 15-70% by weight anhydrosugar-based monomers and 30-70% by weight of vinyl ester resin and/or unsaturated polyester monomer, with the all weights being based on the weight of the product resin mixture. The unsaturated polyester monomer may be made from one or more of the following components: phthalic acid, terephthalic acid, m-phthalic acid, suberic acid, adipic acid, succinic acid, maleic acid, fumaric acid, butylene glycol, propylene glycol, and ethylene glycol, but is not limited to unsaturated polyesters made therefrom.

Other exemplary compositions comprise 5-95% by weight by weight of anhydrosugar-based monomers, 5-65% by weight of vinyl ester resin monomer and/or unsaturated polyester monomer and 0-50% by weight of at least one reactive diluent, or 15-90% by weight of anhydrosugar-based monomers, 10-55% by weight of vinyl ester resin monomer and/or unsaturated polyester monomer and 0-45% by weight of at least one reactive diluent. The vinyl ester resin is preferably a petroleum-based vinyl ester.

The vinyl ester resins of the present invention are used as monomers and include, but are not limited to, commercial vinyl esters, which are vinyl esters that are commercially available, and which may be derived from any source. A broad range of commercial vinyl esters are suitable for use in the ternary resin systems of the present invention. Some examples of suitable vinyl esters are methacrylated, acrylated glycidyl ethers of bisphenols and novolac vinyl esters. Suitable bisphenols include bisphenol A, hexafluorobisphenol A, bisphenol E, bisphenol F, tetramethyl bisphenol E, tetramethyl bisphenol F, bisphenol M, bisphenol C, bisphenol P and bisphenol Z. Methacrylates and acrylates of ethoxylated bisphenols may also be employed, as well as methacrylates of acrylates of epoxy products.

Vinyl esters with vinyl functionality greater than two may also be employed. Examples include acrylic and alkyl-acrylic vinyl esters of epoxy novolacs, and acrylates of tris-hydroxyphenylmethane glycidyl ether (THPM-GE), ethoxy phenol novolac s, and ethoxylated tris-hydroxyphenylmethane. In addition, brominated versions of the above systems, such as brominated bisphenol A based vinyl esters, may be employed. The preferred vinyl esters for use in the ternary systems of the present invention are the bisphenol vinyl esters due to the desirability of making structural composites from the resultant polymers.

In a ternary resin system, the anhydrosugar-based monomers of the present invention can be added to enhance the Tg of certain resins and/or to adjust the resin viscosity to improve the flow characteristics. The addition of the anhydrosugar-based monomers also increases the sustainability of the resins, and reduces the reliance on reactive diluents, such as styrene, while maintaining or improving on the properties of petroleum-based resins. Use of the anhydrosugar-based monomers in varying concentrations in relation to the petroleum-based vinyl ester and reactive diluents components can allow for the tailoring of the resin properties for specific applications and the tailoring of the properties of polymeric materials that result from these resins.

The resins containing the anhydrosugar-based monomers can be cured using any method that makes use of free-radically initiated reactive curing systems, including, but not limited to thermal cure, room temperature cure, electron beam cure, and ultraviolet cure.

The anhydrosugar-based monomers can be polymerized to form linear, branched, hyperbranched, and cross-linked polymers for a wide array of applications, including biosensors, rheology modifiers, biomaterials, and polymerizable surfactants for media encapsulation. The anhydrosugar-based monomers can also be used for the production of polymer matrix composites, which are used in military, automotive, recreational, and marine applications. Exemplary products that may be made from these polymer matrix composites include body panels and armor for vehicles, composite hoods, and boat hull structures. In addition, these polymer matrix composites can be used with traditional thermosetting vinyl and polyester resins as a gel coating material to provide a protective coating for composites and other surfaces.

The use of anhydrosugar-based monomers as vinyl ester cross-linkers, Tg enhancers and viscosity modulators has been tested experimentally and found to be successful. Thermosetting liquid molding resins using anhydrosugar-based monomers to replace some or all of the petroleum based vinyl ester, or unsaturated polyester resin cross-linkers, blended with common reactive diluents, have also been found to have acceptable resin viscosities and polymer mechanical properties similar to those of commercially available petroleum-based vinyl ester/styrene polymers.

EXAMPLES

The following examples are shown using isosorbide as the starting point of the synthesis of the anhydrosugar-based monomers. The isosorbide may be substituted with either isomannide or isoidide without any affect on the outcome of the reaction, yielding similar resin systems that result in comparable polymer systems.

Example 1

Stoichiometric amounts of isosorbide and triethyl amine were dissolved into dichloromethane and cooled to 0° C. before slowly adding dropwise 2-2.5 molar equivalents of acryloyl chloride or methacryoyl chloride. The reaction mixture was slowly warmed to between 21-30° C. and stirred for an additional 15-24 hours. This reaction was quenched with a saturated solution of sodium bicarbonate and then stirred vigorously for 20-45 minutes before partitioning the layers. The organic solution was sequentially washed with aqueous saturated sodium bicarbonate, water and aqueous saturated sodium chloride, dried over $MgSO_4$ and the solvent was removed under reduced pressure. The product was a pale yellow to light brown oil. $^1H$ NMR analysis showed that the degree of (meth)acrylation was 1.8-2.0 (meth)acrylate groups per molecule.

Example 2

Stoichiometric amounts of isosorbide and triethyl amine were dissolved into dichloromethane before adding a catalytic amount of dimethylaminopyridine (2.0-10.0 mol %) and cooling to 0° C. Once the reaction mixture reached the desired temperature, 2-2.5 molar equivalents of acrylic anhydride or methacrylic anhydride were slowly added dropwise. The reaction mixture was slowly warmed to between 21-30° C. and stirred for an additional 15-24 hours. This reaction was quenched with a saturated solution of sodium bicarbonate and then stirred vigorously for 20-45 minutes before partitioning the layers. The organic solution was sequentially washed with aqueous saturated sodium bicarbonate, 1 M hydrochloric acid, water and aqueous saturated sodium chloride, dried over $MgSO_4$ and the solvent was removed under reduced pressure. The product was a clear-colorless to pale yellow oil. $^1H$ NMR analysis showed that the degree of (meth)acrylation was 1.8-2.0 (meth)acrylate groups per molecule.

Example 3

Isosorbide was melted at 68° C. before adding hydroquinone (0.2 mol %) and 2.0-2.5 molar equivalents of acrylic acid or methacrylic acid. After the addition of a catalytic amount of acid, such as p-toluenesulfonic acid (0.5-2.5 wt %), the reaction temperature was raised to 130-145° C. and the progress followed by acid number titrations. After 18-36 hours, the reaction mixture was cooled to room temperature and dissolved in ethyl acetate. The organic solution was washed sequentially with aqueous saturated sodium bicarbonate, water and aqueous sodium chloride and dried over $MgSO_4$. The solvent was removed under reduced pressure and the product appeared as a pale yellow to light brown oil. $^1H$ NMR analysis showed that the degree of (meth)acrylation was 1.7-2.0 (meth)acrylate groups per molecule.

Example 4

Isosorbide and 2-2.5 molar equivalents of either methyl acrylate or methyl methacrylate were melted together at 68° C. before adding a free radical inhibitor (0.1 mol % of hydroquinone), and a catalytic amount of acid, such as p-toluenesulfonic acid (1.0-3.5 mol %). The temperature was raised to, and maintained at 85° C. for 5-10 hours or until the reaction was complete. The product's appearance varied from a light to dark brown oil. $^1H$ NMR analysis showed that the degree of (meth)acrylation was 1.5-1.8 (meth)acrylate groups per molecule.

Example 5

Isosorbide was heated at 60° C. until a homogeneous melt was formed before adding epichlorohydrin (2.0-4.0 molar equivalents) and stirring at 100° C. for 4-6 hours. 50% aqueous sodium hydroxide (2.0-4.0 molar equivalents) was added to the pale yellow reaction mixture and the reaction mixture was stirred for an additional 3-5 hours. The sodium chloride byproduct that precipitated out of solution formed a thick paste which was separated by filtration. The remaining yellow liquid was dissolved in diethyl ether and the organic solution washed with water, dried over MgSO$_4$ and condensed under reduced pressure to yield the product as a pale yellow oil. $^1$H NMR analysis showed signals in the expected ranges. In addition, epoxide titrations completed in accordance with ASTM 1652-04 showed that the resulting structures possessed 1.4-1.9 epoxy groups per molecule. This example produced Known 1 shown in FIG. 1.

Example 6

A stirred solution of Known 1 and either acrylic acid or methacrylic acid (2.0-2.5 molar equivalents) with a catalytic amount of AMC-2™ (Aerojet chemicals, 2.5-10 mole % based on Known 1) was heated to 100° C. for 2-5 hours. The reaction mixture was cooled to room temperature. The resulting blue-green product was characterized by $^1$H NMR. Analysis showed that there were 1.8-2.0 (meth)acrylate groups per molecule.

Example 7

Known 1 and either acrylic acid or methacrylic acid (2.0-2.2 mole equivalents) were dissolved in acetonitrile and refluxed with a catalytic amount of tetrabutylammonium bromide (TBAB, 5-20 mole % based on isosorbide) for 3-8 hours. The reaction progress was followed by acid number titrations. The reaction mixture was then cooled and the acetonitrile removed under reduced pressure. The resulting oil was dissolved in ethyl acetate and the organic solution was washed sequentially with water, aqueous saturated sodium bicarbonate and aqueous saturated sodium chloride, dried over magnesium sulfate and concentrated under reduced pressure. The product appeared as a light yellow to light brown oil. $^1$H NMR analysis showed that there were 1.75-1.9 (meth)acrylate groups per molecule.

Example 8

Known 0 and either glycidyl acrylate or glycidyl methacrylate (2.0-2.2 mole equivalents) were mixed together and gently heated to 45-65 C before adding Tin (II) fluoride (SnF$_2$, 2-6 wt %). The reaction was stirred for 12-24 hours and over the course of the reaction the solid Known 0 became soluble and a homogenous solution was formed. At the end of the reaction, the Tin (II) fluoride was allowed to settle to the bottom of the reaction vessel and the resin was separated by decantation. The product appeared as a colorless to pale yellow, tacky, viscous gel. $^1$H NMR analysis showed 1.85-2.0 glycidyl(meth)acrylate groups per molecule.

Example 9

Isosorbide and hydroquinone (0.1 wt %, based on isosorbide) were heated to 70° C. until a homogeneous melt was formed. Freshly pulverized maleic anhydride (2-2.5 molar equivalents) was slowly added portionwise to this bright yellow solution. The reaction mixture was allowed to melt and homogenize over a period of 15-35 minutes. The reaction temperature was raised to 87-95° C. and dimethylbenzyl amine (DMBA, 1.0 wt %, based on isosorbide) catalyst was slowly added dropwise. The reaction mixture was stirred vigorously for 2-5 hours while maintaining the reaction temperature between 87-95° C. At the conclusion on the reaction, the product was cooled to room temperature and appeared as a viscous, hard yellow gel. $^1$H NMR analysis showed that there were 1.8-2.0 maleate groups per molecule.

Example 10

Product 6 was softened at 70° C. before adding glycidyl acrylate or glycidyl methacrylate (2.0-2.02 molar equivalents) and a catalytic amount of AMC-2™ (Aerojet chemicals, 2.5-10 mole % based on the moles of Product 6). The temperature was maintained at 70° C. for 4-6 hours before allowing the reaction to cool to room temperature. The resulting emerald colored viscous gel was characterized by $^1$H NMR and found to have 1.9-2.0 glycidyl(meth)acrylate groups per molecule.

Example 11

Product 6 and either glycidyl acrylate or glycidyl methacrylate (2.0-2.2 mole equivalents) were dissolved in acetonitrile and refluxed with a catalytic amount of tetrabutylammonium bromide (TBAB, 5-20 mole % based on isosorbide) for 3-8 hours. The progress of the reaction was followed by acid number titrations. The reaction mixture was then cooled and the acetonitrile removed under reduced pressure. The resulting oil was dissolved in ethyl acetate and the organic solution was washed sequentially with water, aqueous saturated sodium bicarbonate and aqueous saturated sodium chloride and dried over magnesium sulfate and concentrated under reduced pressure. The product appeared as a light yellow to light brown oil. $^1$H NMR analysis showed 1.7-2.0 glycidyl(meth)acrylate groups per molecule.

Example 12

Neat monomer with a chemical structure similar to a vinyl ester, i.e. Product 2, was free-radically polymerized by the addition of 0.375 wt % Cobalt Naphthanate (CoNap) and 1.5 wt % Trigonox 239 A (Trigonox). The neat resin was purged with nitrogen prior to the addition of initiator and promoter for approximately 15 minutes to prevent oxygen inhibition during curing. The purged resin mixture with added initiator and promoter were poured into a silicone mold and allowed to cure at room temperature inside an oven with a constant low flow of nitrogen to avert oxygen inhibition.

Example 13

Neat monomer with chemical structure similar to polyester resin, i.e. Product 8, was free-radically polymerized with the addition of 0.375 wt % Cobalt Naphthanate (CoNap) and 1.5 wt % methyl ethyl ketone peroxide (MEKP). The neat resin was purged with nitrogen prior to the addition of initiator and promoter for approximately 15 minutes to prevent oxygen inhibition during curing. The purged resin mixture with added initiator and promoter were poured into a silicone mold and allowed to cure at room temperature inside an oven with a constant low flow of nitrogen to avert oxygen inhibition.

Example 14

The rheological and thermomechanical properties of Product 2 were tested as a neat monomer. Product 2 exhibited a Newtonian viscosity of approximately 120 cP at 25° C. Following curing by the procedure described in Example 12, the cured monomer was free-radically polymerized at room temperature and post cured at 180° C. for 2 hours. Dynamic Mechanical Analysis (DMA) showed a Tg of approximately 250° C. and a storage modulus of 2,900 MPa at 25° C.

Example 15

A partial bio-based monomer blend was formulated in a ratio of 35:65 wt % of styrene, as a reactive diluent, to Product 2, as a cross-linker, respectively. The formulated monomer blend had a Newtonian viscosity of 5 cP at 25° C. Following curing by the procedure described in Example 12, the cured monomer blend was free-radically polymerized at room temperature and post cured at 190° C. for 2 hours. DMA results showed a Tg of approximately 212° C. and a storage modulus of 3,234 MPa at 25° C.

Example 16

A partial bio-based three-component monomer blend was formulated in a ratio of 10:80:10 wt % of Product 2, methacrylated epoxy RDX 26936 (RDX), as a vinyl ester resin mixture, and styrene, as a reactive diluent, respectively. The formulated monomer blend had a Newtonian viscosity of 8,981 cP at 25° C. Following curing by the procedure described in example 12, the cured monomer blend was free-radically polymerized at room temperature and post cured at 190° C. for 2 hours. DMA results showed a Tg of approximately 145° C. and a storage modulus of 2,893 MPa at 25° C.

Example 17

A partial bio-based three-component monomer blend was formulated in a ratio of 50:40:10 wt % of Product 2, RDX, as a vinyl ester resin mixture, and styrene, as a reactive diluent, respectively. The formulated three-component monomer blend had a Newtonian viscosity of 480 cP at 25° C. Following curing by the method described in example 12, the cured monomer blend was free-radically polymerized at room temperature and post cured at 200° C. for 2 hours. DMA results showed a Tg of approximately 169° C. and a storage modulus of 2,893 MPa at 25° C.

Example 18

A partial bio-based three-component monomer blend was formulated in a ratio of 80:10:10 wt % of Product 2, RDX, as a vinyl ester resin mixture, and styrene, as a reactive diluent, respectively. The formulated three-component monomer blend had a Newtonian viscosity of 68 cP at 25° C. Following curing by the method described in example 12, the cured monomer blend was free-radically polymerized at room temperature and post cured at 190° C. for 2 hours. DMA results showed a Tg of approximately 244° C. and a storage modulus of 3,352 MPa at 25° C.

Example 19

A bio-based monomer blend was formulated in a ratio of 35:65 wt % of furfuryl methacrylate, as a reactive diluent, to Product 2, as a cross-linker, respectively. The formulated monomer blend had a Newtonian viscosity of 16 cP at 25° C. Following curing by the method described in example 12, the cured monomer blend was free-radically polymerized at room temperature and post cured at 145° C. for 2 hours. DMA results showed a Tg of approximately 122° C. and a storage modulus of 3,421 MPa at 25° C.

Example 20

A bio-based three-component monomer blend was formulated in a ratio of 10:80:10 wt % of Product 2, RDX, as a vinyl ester resin mixture, and furfuryl methacrylate, as a reactive diluent, respectively. The formulated three-component monomer blend had a Newtonian viscosity of 22,830 cP at 25° C. Following curing by the procedure described in example 12, the cured monomer blend was free-radically polymerized at room temperature and post cured at 170° C. for 2 hours. DMA results showed a Tg of approximately 128° C. and a storage modulus of 3,404 MPa at 25° C.

Example 21

A bio-based vinyl ester ternary monomer system was formulated in a ratio of 50:40:10 wt % of Product 2, RDX, as a vinyl ester resin mixture, and furfuryl methacrylate respectively. The formulated monomer blend had a Newtonian viscosity of 701 cP at 25° C. Following curing by the procedure described in example 12, the cured, bio-based three-component monomer blend was free-radically polymerized at room temperature and post cured at 195° C. for 2 hours. DMA results showed a Tg of approximately 157° C. and a storage modulus of 3,525 MPa at 25° C.

Example 22

A bio-based vinyl ester three-component monomer blend was formulated in a ratio of 80:10:10 wt % of Product 2, RDX, as a vinyl ester resin mixture, and furfuryl methacrylate respectively. The formulated three-component monomer blend had a Newtonian viscosity of 92 cP at 25° C. Following curing by the procedure described in example 12, the cured, bio-based three-component monomer blend was free-radically polymerized at room temperature and post cured at 190° C. for 2 hours. DMA results showed a Tg of approximately 263° C. and a storage modulus of 3,455 MPa at 25° C.

Example 23

A bio-based two-component monomer blend was formulated in a ratio of 35:65 wt % of methacrylated lauric acid (MLau) to Product 2 respectively. The formulated monomer blend had a Newtonian viscosity of 73 cP. Following curing by the method described in example 12, the cured, bio-based two-component monomer blend was free-radically polymerized at room temperature and post cured at 110° C. for 2 hours. DMA results showed a Tg of approximately 107° C. and a storage modulus of 2,220 MPa at 25° C.

Example 24

A bio-based vinyl ester three-component monomer blend was formulated in a ratio of 10:80:10 wt % of Product 2, RDX, as a vinyl ester resin mixture, and MLau respectively. The formulated three-component monomer blend had a Newtonian viscosity of 58,995 cP at 25° C. Following curing by the procedure described in example 12, the cured, bio-based three-component monomer blend was free-radically polymerized at room temperature and post cured at 160° C.

for 2 hours. DMA results showed a Tg of approximately 169° C. and a storage modulus of 3,322 MPa at 25° C.

Example 25

A bio-based vinyl ester three-component monomer blend was formulated in a ratio of 50:40:10 wt % of Product 2, RDX, as a vinyl ester resin mixture, and MLau respectively. The formulated three-component monomer blend had a Newtonian viscosity of 1,445 cP at 25° C. Following curing by the procedure described in example 12, the cured, bio-based three-component monomer blend was free-radically polymerized at room temperature and post cured at 180° C. for 2 hours. DMA results showed a Tg of approximately 165° C. and a storage modulus of 3,206 MPa at 25° C.

Example 26

A bio-based vinyl ester three-component monomer blend was formulated in a ratio of 80:10:10 wt % of Product 2, RDX, as a vinyl ester resin mixture, and MLau respectively. The formulated three-component monomer blend had a Newtonian viscosity of 153 cP at 25° C. Following curing by the procedure described in example 12, the cured, bio-based three-component monomer blend was free-radically polymerized at room temperature and post cured at 125° C. for 2 hours. DMA results showed a Tg of 193° C. and a storage modulus of 2,927 MPa at 25° C.

Example 27

The rheological and thermomechanical properties of Product 8 were tested as a neat monomer. Product 8 had a Newtonian viscosity approximately 620,125 cP at 25° C. Following curing by the procedure described in example 13, the neat monomer was free-radically polymerized at room temperature and post cured at 110° C. for 2 hours. DMA results showed a Tg of approximately 90° C. and a storage modulus of 3,073 MPa at 25° C.

Example 28

A partial bio-based monomer blend was formulated in a ratio of 35:65 wt % of styrene, as a reactive diluent, to Product 8, as a cross-linker, respectively. The formulated monomer blend had a Newtonian viscosity of 172 cP at 25° C. Following curing by the procedure described in example 13, the cured monomer blend was free-radically polymerized at room temperature and post cured at 110° C. for 2 hours. DMA results showed a Tg of approximately 130° C. and a storage modulus of 3,293 MPa at 25° C.

Example 29

A partial bio-based three-component monomer blend was formulated in a ratio of 80:10:10 wt % of Product 8, RDX, as a vinyl ester resin mixture, and styrene, as a reactive diluent, respectively. The formulated three-component monomer blend had a Newtonian viscosity of 16,115 cP at 25° C. Following curing by the method described in example 13, the cured monomer blend was free-radically polymerized at room temperature and post cured at 110° C. for 2 hours. DMA results showed a Tg of approximately 118° C. and a storage modulus of 3,758 MPa at 25° C.

Example 30

A partial bio-based monomer blend was formulated in a ratio of 35:65 wt % of furfuryl methacrylate, as a reactive diluent, to Product 8, as a cross-linker, respectively. The formulated monomer blend had a Newtonian viscosity of 2,234 cP at 25° C. Following curing by the procedure described in example 13, the cured monomer blend was free-radically polymerized at room temperature and post cured at 110° C. for 2 hours. DMA results showed a Tg of approximately 101° C. and a storage modulus of 3,361 MPa at 25° C.

Example 31

A bio-based three-component monomer blend was formulated in a ratio of 80:10:10 wt % of Product 8, RDX, as a vinyl ester resin mixture, and furfuryl methacrylate, as a reactive diluent, respectively. The formulated three-component monomer blend had a Newtonian viscosity of 45,709 cP at 25° C. Following curing by the procedure described in example 13, the cured monomer blend was free-radically polymerized at room temperature and post cured at 110° C. for 2 hours. DMA results showed a Tg of approximately 126° C. and a storage modulus of 3,044 MPa at 25° C.

Example 32

A bio-based two-component monomer was formulated in a ratio of 35:65 wt % of methacrylated lauric acid (MLau) to Product 8, respectively. The formulated monomer blend had a Newtonian viscosity of 102,351 cP at 25° C. Following curing by the method described in example 13, the cured, bio-based two-component monomer blend was free-radically polymerized at room temperature and post cured at 110° C. for 2 hours. DMA results showed a Tg of approximately 50° C. and a storage modulus of 1,648 MPa at 25° C.

Example 33

A bio-based vinyl ester three-component monomer blend was formulated in a ratio of 80:10:10 wt % Product 8, RDX, as a vinyl ester resin mixture, and MLau respectively. The formulated three-component monomer blend had a Newtonian viscosity of 12,376 cP at 25° C. Following curing by the procedure described in example 13, the cured, three-component monomer blend was free-radically polymerized at room temperature and post cured at 110° C. for 2 hours. DMA results showed a Tg of 87° C. and a storage modulus of 2,916 MPa at 25° C.

Example 34

A partial bio-based monomer blend was formulated in a ratio of 80:20 wt % Product 2, as a viscosity modulator, to Viapal™ 450 Unsaturated Polyester Resin (UPE), as a cross-linker, respectively. The formulated monomer blend had a Newtonian viscosity of 1,098 cP at 25° C. Following curing by the procedure described in example 13, the cured monomer blend was free-radically polymerized at room temperature and post cured at 110° C. for 2 hours. DMA results showed a Tg of approximately 58° C. and a storage modulus of 3,623 MPa at 25° C.

Example 35

A partial bio-based three-component monomer blend was formulated in a ratio of 50:40:10 wt % of Product 8, UPE, as a resin mixture, and styrene, as a reactive diluent, respectively. The formulated three-component monomer blend had a Newtonian viscosity of 2,710 cP at 25° C. Following curing by the method described in example 13, the cured monomer blend was free-radically polymerized at room temperature and post cured at 110° C. for 2 hours. DMA results showed a Tg of approximately 56° C. and a storage modulus of 2,816 MPa at 25° C.

Example 36

A partial bio-based three-component monomer blend was formulated in a ratio of 50:40:10 wt % of Product 2, UPE, as a resin mixture, and furfuryl methacrylate (FM), as a reactive diluent, respectively. The formulated three-component monomer blend had a Newtonian viscosity of 700 cP at 25° C. Following curing by the method described in example 13, the cured monomer blend was free-radically polymerized at room temperature and post cured at 110° C. for 2 hours. DMA results showed a Tg of approximately 140° C. and a storage modulus of 157 MPa at 25° C.

Example 37

A partial bio-based monomer blend was formulated in a ratio of 50:50 wt % of Product 2, as a viscosity modulator, to RDX, as a cross-linker, respectively. Following curing by the procedure described in example 13, the cured monomer blend was free-radically polymerized at room temperature and post cured at 110° C. for 2 hours. DMA results showed a Tg of approximately 130° C. and a storage modulus of 3200 MPa at 25° C.

Example 38

A partial bio-based monomer blend was formulated in a ratio of 80:20 wt % of Product 2, as a viscosity modulator, to RDX, as a cross-linker, respectively. Following curing by the procedure described in example 13, the cured monomer blend was free-radically polymerized at room temperature and post cured at 110° C. for 2 hours. DMA results showed a Tg of approximately 212° C. and a storage modulus of 3100 MPa at 25° C.

It is to be understood, however, that even though numerous characteristics and advantages of the present invention have been set forth in the foregoing description, together with details of the examples/embodiments in this application, the disclosure is illustrative only, and changes may be made by those sufficed in the art in detail, especially in matters of shape, size and arrangement of parts within the principles of the invention to the full extent indicated by the broad general meanings of the terms in which the appended claims are expressed. Accordingly, departures may be made from such details without departing from the spirit or scope of present invention.

What is claimed is:

1. A polymerizable monomer selected from the group consisting of:

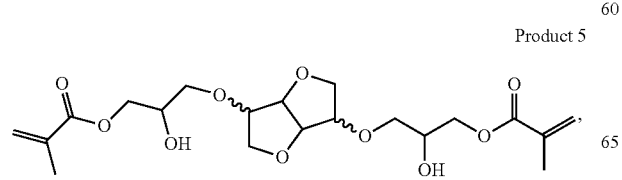
Product 5

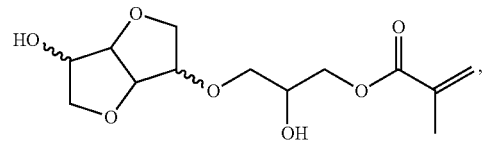
Product 5a

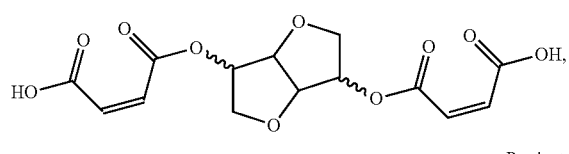
Product 6

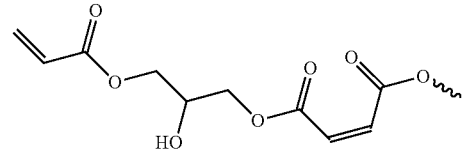
Product 7

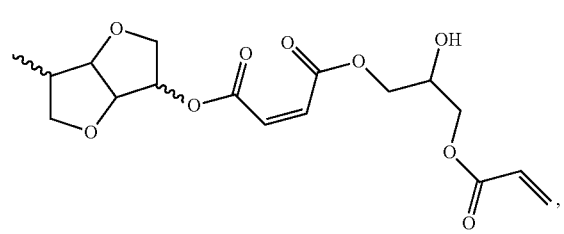

and

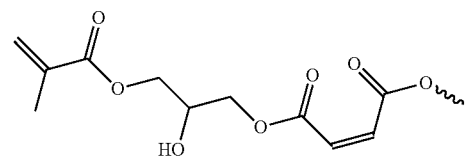
Product 8

2. A polymerizable monomer as claimed in claim 1, wherein the monomer is:

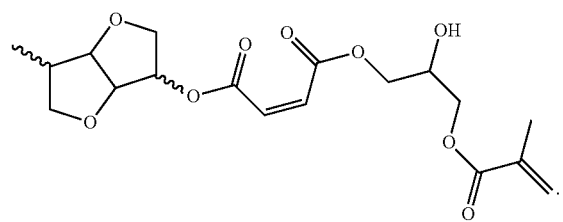
Product 5

3. A polymerizable monomer as claimed in claim 1, wherein the monomer is:

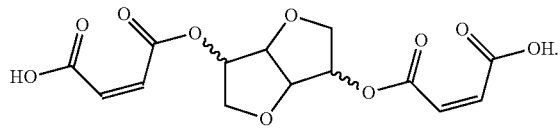

Product 6

4. A polymerizable monomer as claimed in claim 1, wherein the monomer is:

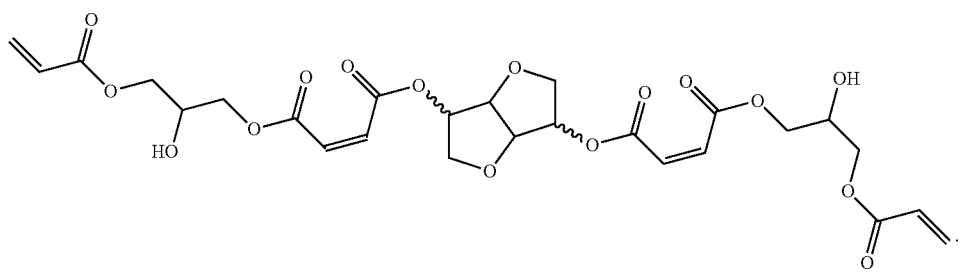 [SMILES: C=CC(=O)OCC(O)COC(=O)/C=C\C(=O)OC1COC2C(OC(=O)/C=C\C(=O)OCC(O)COC(=O)C=C)COC12]

Product 7

5. A polymerizable monomer as claimed in claim 1, wherein the monomer is:

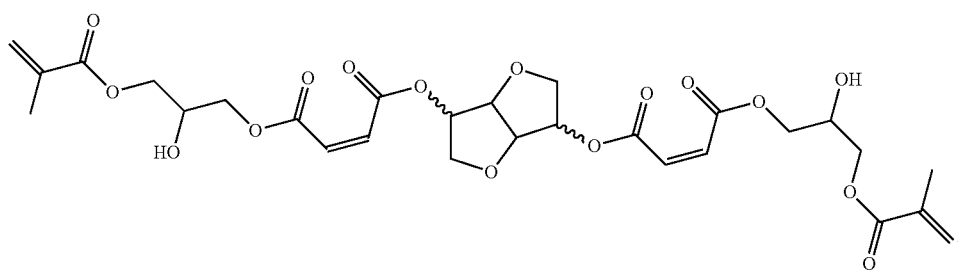

Product 8

6. A polymerizable monomer as claimed in claim 1, wherein the monomer is:

Product 5a

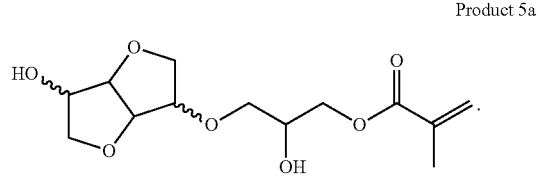 [SMILES: C=C(C)C(=O)OCC(O)COC1COC2C(O)COC12]

7. A copolymer formed by curing a curable composition comprising at least one monomer selected from the group consisting of the polymerizable monomers of claim 1 using a free-radical initiator.

8. The copolymer of claim 7, wherein the curable composition comprises at least one vinyl ester resin monomer and/or at least one unsaturated polyester monomer.

9. The copolymer of claim 8, wherein the curable composition further comprises at least one reactive diluent.

10. The copolymer of claim 8, wherein the curable composition comprises 1-99% by weight of at least one monomer selected from the group consisting of the polymerizable monomers of claim 1, 1-70% by weight of vinyl ester resin monomer and/or unsaturated polyester monomer and 0-60% by weight of at least one reactive diluent.

11. The copolymer of claim 8, wherein the curable composition comprises 5-95% by weight of at least one monomer selected from the group consisting of the polymerizable monomers of claim 1, 10-55% by weight of vinyl ester resin monomer and/or unsaturated polyester monomer and 0-50% by weight of at least one reactive diluent.

12. The copolymer of claim 9, wherein the composition comprises 15-90% by weight of at least one monomer selected from the group consisting of the polymerizable monomers of claim 1, 10-55% by weight of vinyl ester resin monomer and/or unsaturated polyester monomer and 5-45% by weight of at least one reactive diluent.

13. The copolymer of claim 8, comprising a vinyl ester resin monomer selected from the group consisting of (meth)acrylated glycidyl ethers of bisphenols, (meth)acrylated ethoxylated bisphenols and novolac vinyl esters.

14. The copolymer of claim 8, comprising a vinyl ester monomer selected from the group consisting of: bisphenol A, hexafluorobisphenol A, bisphenol E, bisphenol F, tetramethyl bisphenol E, tetramethyl bisphenol F, bisphenol M, bisphenol C, bisphenol P and bisphenol Z.

15. The copolymer of claim 14, wherein the curable composition further comprises a reactive diluent selected from the group consisting of: styrene, 2-hydroxymethacrylate, methyl methacrylate, methyl acrylate, furfuryl methacrylate, methacrylated lauric acid and methacrylated fatty acids.

16. The copolymer of claim 15, wherein the monomer of claim 1 is selected from a monomer of the formula 5 and a monomer of the formula 5a.

17. The copolymer of claim 15, wherein the monomer of claim 1 is selected from a monomer of the formula 7 and a monomer of the formula 8.

18. The copolymer of claim 8, wherein the curable composition comprises an unsaturated polyester monomer made from one or more of the following components: phthalic acid, terephthalic acid, m-phthalic acid, suberic acid, adipic acid, succinic acid, maleic acid, fumaric acid, butylene glycol, propylene glycol, and ethylene glycol.

19. The copolymer of claim 18, wherein the curable composition further comprises a reactive diluent selected from the group consisting of: styrene, 2-hydroxymethacrylate, methyl methacrylate, methyl acrylate, furfuryl methacrylate, methacrylated lauric acid and methacrylated fatty acids.

20. The copolymer of claim 19, wherein the monomer of claim 1 is selected from a monomer of the formula 5 and a monomer of the formula 5a.

21. The copolymer of claim 19, wherein the monomer of claim 1 is selected from a monomer of the formula 7 and a monomer of the formula 8.

\* \* \* \* \*